United States Patent
Buckner

(10) Patent No.: US 6,802,347 B2
(45) Date of Patent: Oct. 12, 2004

(54) ELECTRONIC FILL FOR WATER JACKETED INCUBATORS

(75) Inventor: Jeff Buckner, Weaverville, NC (US)

(73) Assignee: Kendro Laboratory Products, L.P., Newtown, CT (US)

(*) Notice: Subject to any disclaimer, the term of this patent is extended or adjusted under 35 U.S.C. 154(b) by 58 days.

(21) Appl. No.: 10/300,779

(22) Filed: Nov. 21, 2002

(65) Prior Publication Data

US 2004/0099331 A1 May 27, 2004

(51) Int. Cl.[7] ................................................. B65B 3/00
(52) U.S. Cl. ........................... 141/198; 141/82; 141/1; 222/129; 222/146.2; 222/183
(58) Field of Search ............................... 141/1, 82, 94, 141/198; 222/1, 129, 146.2, 173, 183

(56) References Cited

U.S. PATENT DOCUMENTS

| | | | | |
|---|---|---|---|---|
| 3,980,131 A | * | 9/1976 | Perle et al. | 165/61 |
| 4,762,060 A | * | 8/1988 | Santa Cruz | 99/483 |
| 5,850,942 A | * | 12/1998 | DeSimone et al. | 222/146.5 |
| 2003/0033872 A1 | * | 2/2003 | Adkins et al. | 73/323 |

* cited by examiner

Primary Examiner—J. Casimer Jacyna
(74) Attorney, Agent, or Firm—Baker & Hostetler LLP

(57) ABSTRACT

An apparatus and method is provided to fill liquids in a water jacket of an enclosed chamber. A valve, such as a solenoid can be actuated remotely to open and allow liquids to fill the water jacket. A sensor, such as a fill level sensor can sense and can communicate the amount of liquid in the water jacket to a controller. The controller or an actuator can be used to actuate the solenoid. The controller can actuate the solenoid at a period of time, at an event or at any other desired time.

30 Claims, 3 Drawing Sheets

Open

Closed

ELECTRONIC FILL FOR WATER JACKETED INCUBATORS

FIELD OF THE INVENTION

Embodiments of the present invention generally relate to an apparatus and method for use with a controlled gas atmosphere. More particularly, the apparatus and method of the present invention relates to an electronic fill in a water jacketed incubator.

BACKGROUND OF THE INVENTION

There are a number of commercial applications that utilize a controlled gas atmosphere enclosure. For example, in the semiconductor industry, gases are injected into an enclosed chamber, wherein one of the gases is plasmarized and strikes a target on a chamber lid causing the target's materials to deposit on a wafer. Other commercial applications include using controlled gases to cultivate biological cultures in an enclosed chamber, such as an incubator.

It is desirable to maintain optimal conditions inside the incubator in order to promote the desired growth of the cultures. In a conventional incubator, gasses such as $O_2$, $N_2$, and $CO_2$ are introduced from their respective tanks into the chamber depending on the growing conditions desired. Typically, the user sets the $CO_2$ and $O_2$ setpoints and appropriate gases are added or depleted to reach the setpoints.

Most biological incubators are either forced draft or water jacket. In the forced draft incubator, the inner space is lined with insulation instead of a water jacket. Heating of the chamber is provided by having a duct, a fan, and a heating element within the chamber. The air is typically circulated by the fan and heated by the heating element within the duct. The air is blown with more force than in the water jacket incubators in order to have more uniform circulation of the air and thus, the temperature in the chamber is uniform.

A water jacket incubator has a jacket that surrounds an inner chamber of the incubator. The water jacket is filled with water and heated to the desired temperature. Typically, the water jacket is filled manually and requires time away from experiments by the researcher. Additionally, because the water jacket is filled manually, over-filling can occur.

Therefore, there is a need for an apparatus and method to quickly fill the water jacket of an incubator with the desired liquid. Additionally, there is a need for an incubator that can be filled with the liquid to the desired level and not over-fill.

SUMMARY OF THE INVENTION

The present invention generally relates to an apparatus and method to fill a water jacketed incubator with liquids. An embedded control system is used to open and close the fill port with a valve, such as a solenoid. The solenoid can be opened by actuating a switch or a control button on the user interface panel. The solenoid can also be opened and closed automatically by the control system. Additionally, a sensor, such as a fill level sensor, is in communication with the control system and can measure when the liquid is at the desired fill level so that the water jacket does not over-fill.

In one embodiment of the present invention, a filling apparatus for an enclosed chamber may include a water jacket that can surround an inner chamber of the enclosed chamber, a controller that can control the operation of the enclosed chamber, and a valve that can be communication with the water jacket and the controller, said valve can allow liquids to fill the water jacket. The filling apparatus can further include an actuator that when actuated can open or can close the valve. The actuator can be a switch, a control button, other actuating device, and a combination thereof and the actuator can be manually actuated. The filling apparatus can also include a sensor that can sense the amount of liquid in the water jacket and that can be in communication with the controller. The sensor can communicate the amount of liquid in the incubator with the controller so that the controller can open the valve to fill the water jacket or can close the valve to stop filling the water jacket. The sensor can be a fill level sensor and the valve can be a solenoid. The controller can be in communication with the valve and can open or close the valve based on a period of time. The period of time can be every hour, everyday, every other day, once a week, every other week, at the end of the shift, at the beginning of the shift, at a maintenance period, other time periods and a combination thereof. The controller can open or close the valve based on an event and the event can be before or after the first batch of samples is run, before or after the last batch of samples are run, before or after two batches are run, before or after three batches are run or before or after any other events that is desired by the operator, and a combination thereof. When the valve is opened liquid is allowed to fill the water jacket and when the valve is closed liquid is not allowed to fill the water jacket.

In another embodiment, a method of filling liquids into an enclosed chamber is provided and can include filling a water jacket with a liquid, said water jacket surrounds an inner chamber of the enclosed chamber, and controlling the filling of the water jacket with a valve that can be in communication with the water jacket. The method of filling can further include controlling the valve with a controller, measuring the amount of liquid in the water jacket with a sensor, and communicating the amount of liquid in the water jacket to the controller. Communicating the amount of liquid to the controller so that the controller can open or close the valve and controlling the filling can be done by the controller opening or closing the valve. The method of filling liquids can further include actuating the valve with an actuator, wherein the actuator can communicate with the valve to open or close.

In still another embodiment, a filling system for an enclosed chamber means can include a means for filling a containing means with a liquid, said containing means can surround an inner chamber means of the enclosed chamber means, and a means for controlling the filling of the containing means that can be in communication with the means for filling. The filling system can further include a means for sensing the amount of liquid in the containing means, and a means for actuating the means for filling, wherein the means for filling, the means for controlling, means for sensing and the means for actuating can be in communication with each other. The means for filling can be opened or closed by the means for controlling. The means for sensing can communicate the amount of the liquid to the means for controlling so that the means for controlling can open or close the means for filling, as needed. The means for actuating can open or close the means for filling and can be selected from a switch means, a control button, other control means and a combination thereof. The means for filling can be a solenoid and the means for sensing can be a fill level sensor. The means for controlling with the means for actuating can actuate the means for filling based on a period of time or an event. The period of time can be every hour, everyday, every other day, once a week, every other week, at the end of the shift, at the beginning of the shift, at a maintenance period, other time periods and a combination thereof and the event can be before or after the first batch of samples is run, before or after the last batch of samples are run, before or after two batches are run, before or after three batches are run or before or after any other events that is desired by the operator, and a combination thereof.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The present invention allows an operator to fill liquids in a water jacket of an incubator via a valve that is controlled by an actuator such as a switch or a control button, or a controller. The actuator and the controller control the valve, such as a solenoid, that can be opened to allow the liquid to fill the water jacket or can be closed when the water jacket is filled. A fill sensor senses or measures the amount of liquid in the water jacket.

Figure 1:
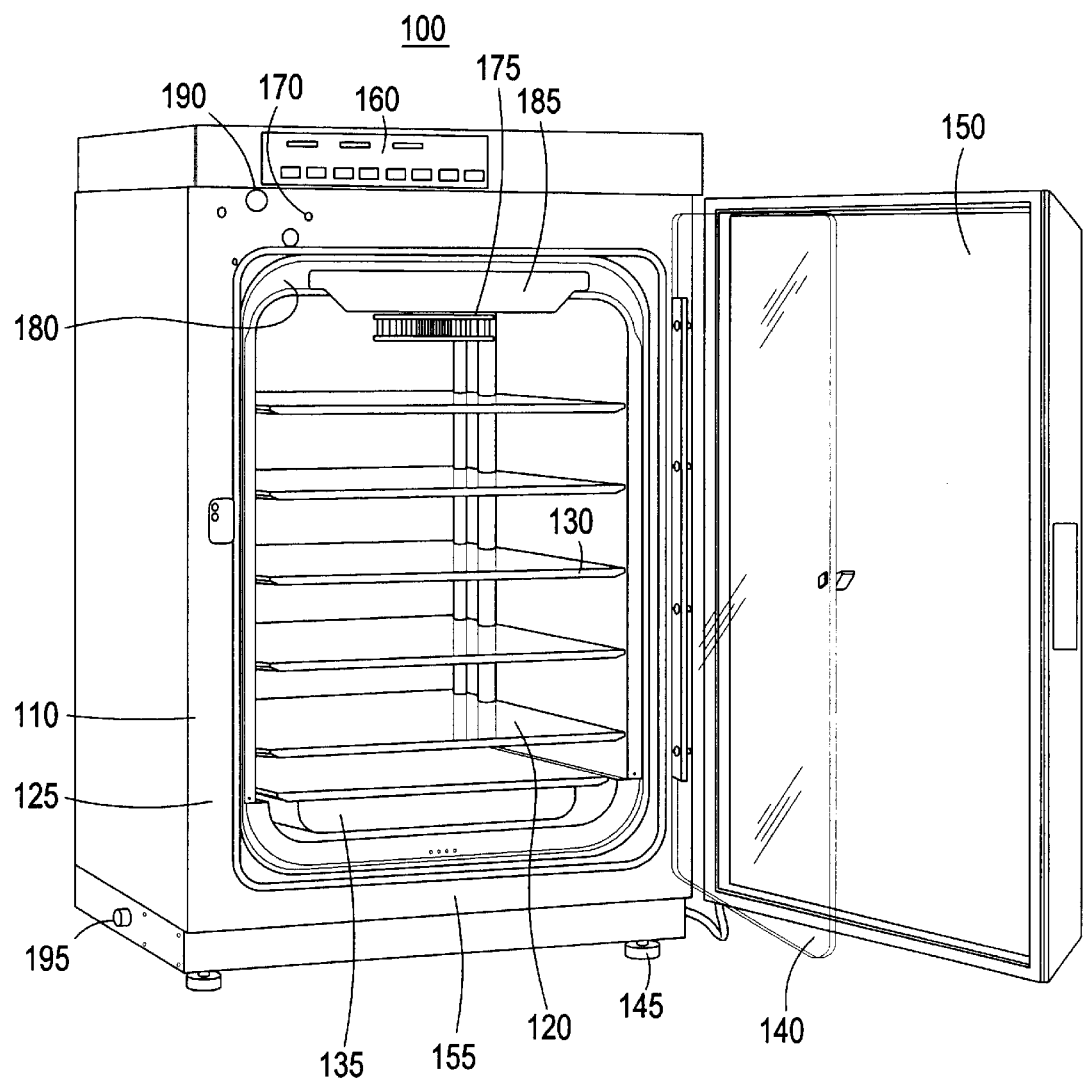
FIG. 1 illustrates a water jacket incubator.

FIG. 1 illustrates a water jacket incubator 100. The incubator 100 includes a cabinet 110, an interior chamber 120, a control system 160 and an outer door 150. The cabinet 110 has a set of leveling feet 145 to adjust the height or level of the incubator 100. The cabinet 110 contains the water jacket 125 (also shown in FIG. 3 at 380), which surrounds the interior chamber 120. The water jacket 125 is filled with a liquid, such as water, and is heated by a heater 155. The water in turns heats an air flow chamber (FIG. 3 at 395) where air can be circulated by an air pump 175. Because water can be heated evenly, the water jacket 125 can evenly distribute the desired heat throughout the interior chamber 120. Such even heating is desired in order to provide a uniform temperature (for the biological cultures) throughout the chamber 120 and to prevent "cold spots," which can cause condensation on the inner chamber walls.

The interior chamber 120 includes a humidity pan 135 that is filled with a liquid, such as water, and provides moisture for the samples that are placed on a set of shelves 130. The shelves 130 are adjustable, as well as removable. A humidity sensor 180 monitors the a mount of humidity in the chamber 120 so that adjustments can be made depending on the nature of the desired culture growth. A $CO_2$ sensor 185 located in the interior chamber 120 monitors the current $CO_2$ levels so that $CO_2$ can be replenished, as needed.

The control system 160 is provided on the cabinet 110 and includes an alarm system, a monitor system, and a user interface. The outer door 150 and an inner glass door 140 provide access to the interior of the cabinet 110. The cabinet 110 has built-in sample port 170 and a fill port 190. The sample port 170 allows an operator (who can also be a researcher) to take samples of the atmosphere and other conditions in the interior chamber 120. The fill port 190 allows the operator to fill the water jacket 125 with water or other liquids. The water can be drained at the lower portion of the cabinet 110 at a drain cap 195.

In order to fill the water jacket 125, a hose (not shown) connected to a liquid source has to be hooked up to the fill port 190. The operator has to wait until the water jacket 125 is filled and then remove the hose. When the hose is removed, the liquid can spill out of the fill port 190 and onto the ground because the operator has over-filled the water jacket 125. The operator then has to "mop up" the liquid in order to prevent others from slipping on the liquid and incurring additional costs of water usage. The "mop up" time makes the operator lose valuable research time. Additional valuable time is also wasted because the operator has to manually hook up the hose, turn the liquid dispenser on, wait for the water jacket 125 to fill (and hopefully not over fill), turn off the liquid dispenser, and then unhook the hose before the experiments can begin.

Figure 2A:
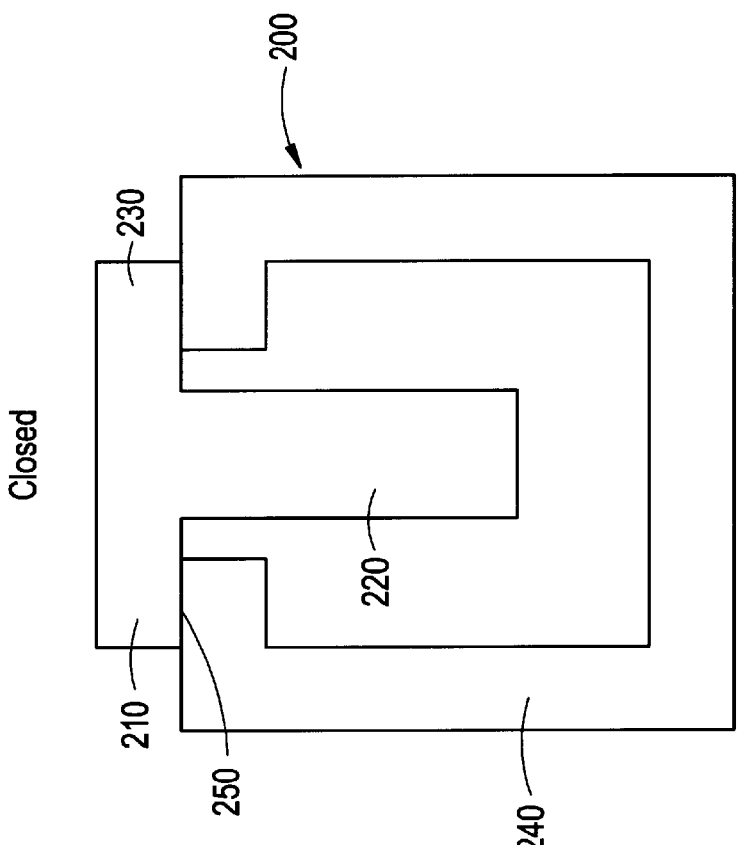
FIG. 2A and FIG. 2B illustrates an embodiment of a solenoid of the present invention.
Figure 2B:
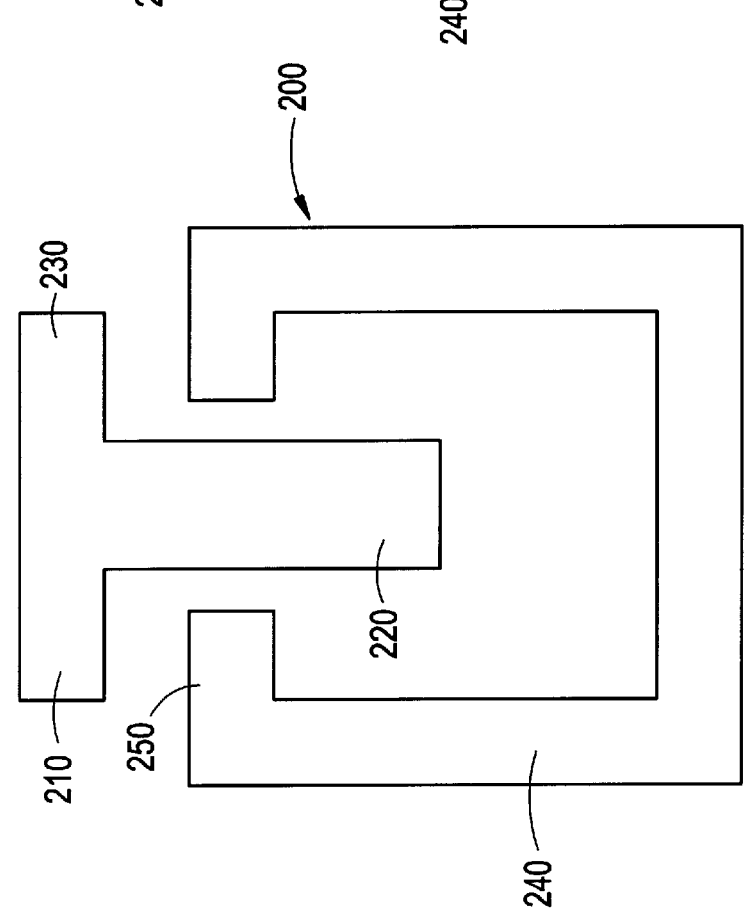

FIG. 2A and FIG. 2B illustrate an embodiment of a solenoid 200 of the present invention. In one embodiment of the invention, the solenoid 200 can be used to fill the liquid into the water jacket. In FIG. 2A, the solenoid is shown in the open position. The solenoid 200 is an electromagnet that includes a coil 240 and a plunger 210. The coil 240 is made up of many "C" stacks, which when current flows through it, creates a magnetic field. The C stacks helps to concentrate the magnetism where it is desired.

The plunger 210 has an upper portion 230 and a lower portion 220. The upper portion 230 can provide a seal with an upper surface 250 of the coil 240. The plunger 210 is typically made from iron (or other conductive material) which is an excellent conductor. Normally, the plunger 210 is "repelled" from the coil 240 due to the magnetic field of the coil being the same polarity as the plunger (both can be positive). The plunger 210 is "pulled in" when current passes through the coil 240 and the polarity of the coil's magnetic field is reversed (see FIG. 2B). Because the plunger 210 is in the opened position, the plunger allows fluids to pass through it.

In FIG. 2B, the solenoid 200 is shown in the closed position. Current is applied to the coil 240, causing a change in the polarity of the magnetic field (change to negative) of the coil. Because the polarity has changed (to negative) in the coil 240, the plunger 210 (being positive) and the upper portion 230 are "pulled in" towards the coil 240. The upper portion 230 creates a tight seal with the upper surface 250. The seal does not allow any liquids to flow through the solenoid 200.

Figure 3:
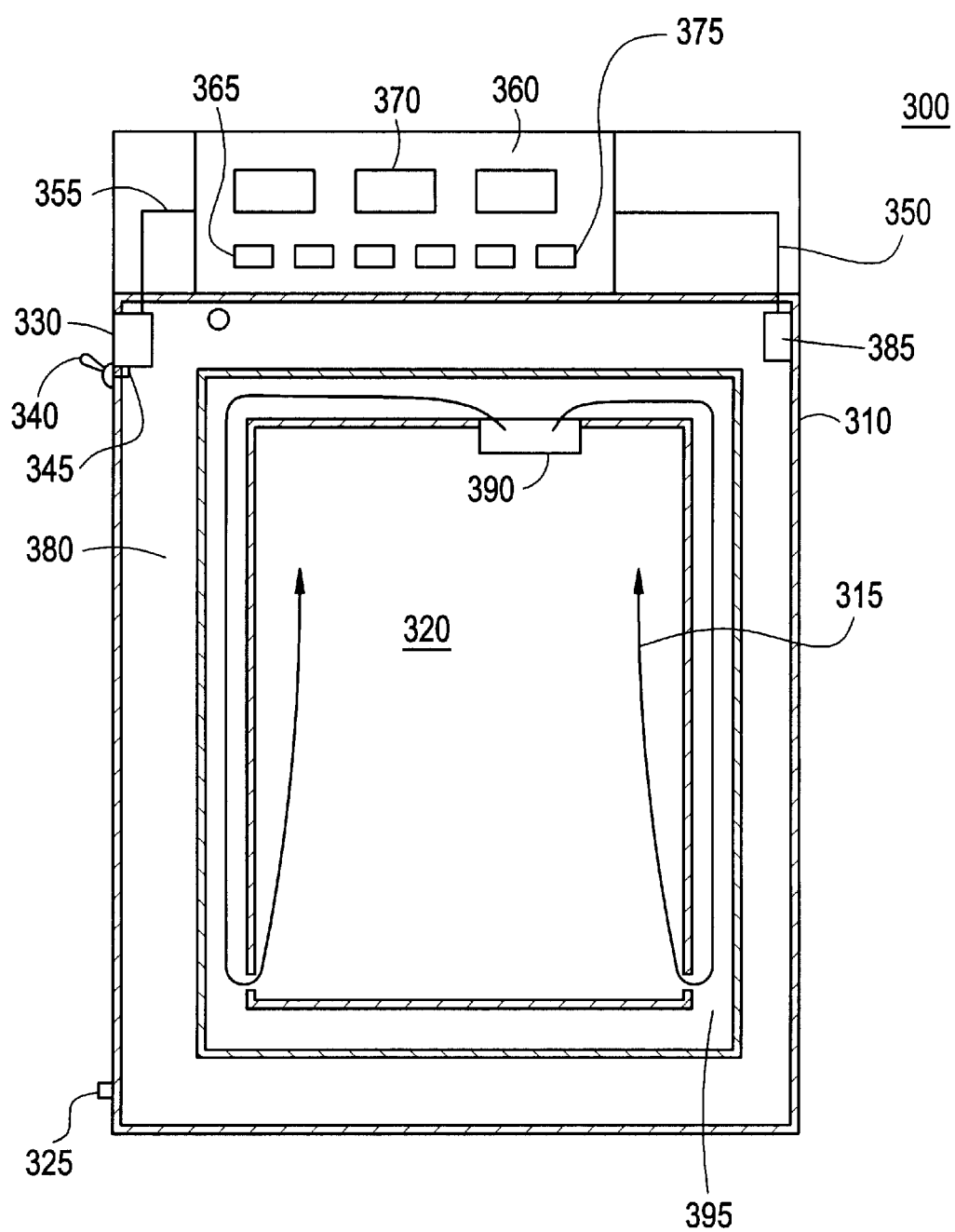
FIG. 3 illustrates the incubator with the solenoid.

FIG. 3 illustrates the incubator 300 with the solenoid 330. In one embodiment of the invention, the incubator 300 includes a cabinet 310 having an interior chamber 320. A water jacket 380 surrounds the interior chamber 320 and can be filled with a liquid. The cabinet includes a control system 360 having at least one or more display 370 and a user interface 365. The control system 360 can control all aspects and operating parameters of the incubator 300 through a microprocessor.

The process as described herein may be controlled by one of any form of general purpose computer processor that can be used in an industrial setting for controlling various chambers and incubators. The control system 360 may use any suitable microprocessor, memory, such as random access memory, read only memory, floppy disk drive, hard disk, or any other form of digital storage, local or remote. Various support circuits may be coupled to the control system 360 for supporting the processor in a conventional manner. Software routines, as required, may be stored in the memory or executed by a second control system that is remotely located.

The control system 360 can control the operating temperature of the incubator 300 by monitoring the temperature in the interior chamber 320 and controlling the heater (not shown). The control system 360 can also control the gas levels in the interior chamber 320, such as the $CO_2$ level and the $O_2$ level, by monitoring and controlling the amount and type of gas that is injected into the interior chamber. The control system 360 also includes one or more displays 370, which includes visual and audible information. The displays 370 can provide information such as door open, current gas levels, setpoints of the gases, the temperature, humidity level and other useful information. The control system 360 also includes a control button 375, which can electronically actuate a solenoid 330.

The solenoid 330 is shown located near or at the upper portion of the water jacket 380. By being at the upper portion of the water jacket 380, it is easier to fill. The solenoid 330 can be located at any position of the incubator that the operator desires. The solenoid 330 can also be the type previously described above. The solenoid 330 can have an interface that connects to a hose (not shown) that supplies the fluid under pressure. The hose can be hooked up when needed or preferably, is continuously hooked up. By having the hose hooked up to the solenoid at all times, liquid can be available for filling when desired.

The solenoid 330 is in communication with the control system 360 via a wireline 355. The wireline 355 can provide a communication link and/or power to the solenoid 330. The control button 375 is in communication with the control system 360, which together or each alone can actuate the solenoid 330 to open or close. When the operator desires to fill the water jacket 380, he can actuate the solenoid 330 with the control button 375. When the solenoid 330 is actuated, it can open and allow the liquid to fill the water jacket 380. As stated above, the solenoid 330 is open because the polarity of the solenoid changed (due to current being shut-off) causing the plunger to be repelled from the solenoid. The control system 360 can keep the solenoid 330 open until the operator again actuates the solenoid with the control button 375 to close it. The solenoid 330 closes because the polarity of the solenoid was reversed when current is introduced and pulled in the plunger 210 causing it to seal with the solenoid. Because the solenoid 330 can open and close by the operator (with the hose connected), the water jacket can be filled easily and quickly so that the operator does not have to waste time to hook the hose, turn on the liquid dispenser, fill the water jacket, turn off the liquid dispenser, and unhook the hose. The actuating button 375 is conveniently located, as part of the control system, so that the operator can easily actuate the solenoid and continue the experiment without wasting time.

In an alternate embodiment, the control button 375 is in direct communication with the solenoid 330 and can actuate it without the assistance of the control system 360. When the operator wants to fill the water jacket 380 he can manually actuate the solenoid to open with the control button 375. After the operator fills the water jacket 380, he can manually actuate the solenoid to close with the control button 375.

The solenoid 330 is exemplary of possible solenoids and other devices performing the same function of the solenoid can be used in the embodiments of the invention. Although the solenoid 330 is preferably an electronic valve, any valve that opens and closes so that liquids can fill the water jacket can be used. Additionally other types of solenoids that are not electronically based can be used.

In another embodiment, the control system 360 can be programmed to open and close the solenoid 330. The control system 360 can be programmed to open to fill the water jacket 380 with liquids or to close and stop filling the water jacket at a set of period of time, after or before an event occurs, or other parameters desired by the operator. The period of time can be every hour, everyday, every other day, once a week, every other week, at the end of a shift (so that incubator can be ready to operate at the next shift), at the beginning of the shift, at a maintenance period, or any other period that is desired by the operator. The solenoid can be actuated after an event, such as before or after the first batch of samples is run, before or after the last batch of samples are run, before or after two batches are run, before or after three batches are run or before or after any other events that is desired by the operator. By having the control system 360 automatically actuate the solenoid (open or close) at a given time period or before or after an event, the operator can have more time to do other things, such as preparing the samples to be run.

In still another embodiment, a switch 340, such as a toggle switch, can be used to actuate the solenoid 330. The switch 340 is in communication with the solenoid 330 via a wireline 345. Similar to wireline 355, wireline 345 can provide a communication link and/or power to the solenoid 330. The switch can actuate the solenoid to the open position and allows the liquid to fill the water jacket 380. In operation, the switch 340 can be "thrown" by the operator by moving in a first direction (cutting off the current) and actuating the solenoid 330 to open. The solenoid 330 can remain open until the switch is moved in a second direction (allowing current to flow) causing the solenoid to close. The switch 340, like the actuating button, can be located in a convenient location for the operator and can be used to open or close the solenoid 330.

The switch 340 and the control button 375 can be located anywhere on the incubator, but preferably, located where it is convenient to the operator, such as shoulder level, or where the operator does not have to bend down in order to reach it. The solenoid can have a self-contained power source so that the switch 340 and control button 375 act like a current gate to allow the current to flow or cut it off. The switch 340 and the control button 375 can be substituted by other devices that can turn the solenoid on and off.

In still another embodiment, a sensing device 385, such as a fill level sensor, is provided to sense the amount of liquid that is in the water jacket 380. The sensing device 385 can be mounted in the interior of the water jacket 380 at a location so that it can sense the liquid level in the water jacket. The sensing device 385 can be in communication with the controller 360 via a wireline 350 (similar to the wirelines above) in order to communicate the liquid level to the controller. The controller 360 and the sensing device 385 can determine the liquid level in the water jacket so that the controller can open (to fill from a liquid source under pressure) and close (stop filling) the solenoid so that the water jacket can be filled, but not over-filled. Because the water jacket is not over-filled, the operator has more time to run more experiments and liquid costs are reduced.

In another embodiment, the sensing device can be operated with the switch 340 and the control button 375. The liquid level in the water jacket 380 can be shown on the display 370. Based on the liquid level, the operator can open (to fill) or close (stop filling) the solenoid 330 to control the amount of liquid in the water jacket 380.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A filling apparatus for an enclosed chamber, comprising:
   an inner air flow chamber that surrounds the enclosed chamber;
   a water jacket that surrounds the inner air flow chamber;
   a heater that heats contents of the water jacket;
   a controller that controls the operation of the inner air flow chamber; and
   a valve located at a top portion of the water jacket that is in communication with the water jacket and the controller, said valve allows liquids to fill the water jacket.

2. The filling apparatus of claim 1, further comprising an actuator that when actuated opens or closes the valve.

3. The filling apparatus of claim 2, wherein the actuator can be selected from a group consisting of a switch, a control button, other actuating device, and a combination thereof.

4. The filling apparatus of claim 2, wherein the actuator can be manually actuated.

5. The filling apparatus of claim 1, further comprising a sensor that senses the amount of liquid in the water jacket and that is in communication with the controller.

6. The filling apparatus of claim 5, wherein the sensor can communicate the amount of liquid in the incubator with the controller so that the controller can open the valve to fill the water jacket when needed.

7. The filling apparatus of claim 5, wherein the sensor can communicate the amount of liquid in the incubator with the controller so that the controller can close the valve to stop filling the water jacket when needed.

8. The filling apparatus of claim 5, wherein the sensor is a fill level sensor.

9. The filling apparatus of claim 1, wherein the valve is a solenoid.

10. The filling apparatus of claim 1, wherein the controller is in communication with the valve and can open or close the valve.

11. The filling apparatus of claim 1, wherein the controller can open or close the valve based on a period of time.

12. The filling apparatus of claim 11, wherein the period of time can be selected from a group consisting of every hour, everyday, every other day, once a week, every other week, at the end of the shift, at the beginning of the shift, at a maintenance period, other time periods and a combination thereof.

13. The filling apparatus of claim 1, wherein the controller can open or close the valve based on an event.

14. The filling apparatus of claim 13, wherein the event can be selected from a group consisting of before or after the first batch of samples is run, before or after the last batch of samples are run, before or after two batches are run, before or after three batches are run or before or after any other events that is desired by the operator, and a combination thereof.

15. The filling apparatus of claim 10, wherein when the valve is opened liquid is allowed to fill the water jacket and when the valve is closed liquid is not allowed to fill the water jacket.

16. A method of filling liquids into an enclosed chamber, comprising the steps of:
   filling a water jacket with a liquid, said water jacket surrounds an inner air flow chamber of the enclosed chamber;
   heating the liquid in the water jacket;
   providing air flow through the inner air flow chamber; and
   controlling the filling of the water jacket with a valve that is in communication with the water jacket.

17. The method of filling liquids of claim 16 further comprising:
   controlling the valve with a controller;
   measuring the amount of liquid in the water jacket with a sensor; and
   communicating the amount of liquid in the water jacket to the controller.

18. The method of filling liquids of claim 17, wherein communicating the amount of liquid to the controller so that the controller can open or close the valve.

19. The method of filling liquids of claim 17, wherein controlling the filling is done by the controller opening or closing the valve.

20. The method of filling liquids of claim 16 further comprising actuating the valve with an actuator, wherein the actuator can communicate with the valve to open or close.

21. A filling system for an enclosed chamber means, comprising:
   a means for filling a containing means with a liquid, said containing means surrounds an inner air flow chamber means of the enclosed chamber means;
   a means for heating the liquid in the containing means;
   a means for providing air flow through the inner air flow means; and
   a means for controlling the filling of the containing means that is in communication with the means for filling.

22. The filling system for the enclosed chamber means of claim 21 further comprising:
   a means for sensing the amount of liquid in the containing means; and
   a means for actuating the means for filling, wherein the means for filling, the means for controlling, means for sensing and the means for actuating are in communication with each other.

23. The filling system for the enclosed chamber means of claim 21, wherein the means for filling can be opened or closed by the means for controlling.

24. The filling system for the enclosed chamber means of claim 22, wherein the means for sensing communicates the amount of the liquid to the means for controlling so that the means for controlling can open or close the means for filling, as needed.

25. The filling system for the enclosed chamber means of claim 22, wherein the means for actuating can open or close the means for filling and can be selected from a group consisting of a switch means, a control button, other control means and a combination thereof.

26. The filling system for the enclosed chamber means of claim 21, wherein the means for filling is a solenoid.

27. The filling system for the enclosed chamber means of claim 22, wherein the means for sensing is a fill level sensor.

28. The filling system for the enclosed chamber means of claim 22, wherein the means for controlling with the means for actuating can actuate the means for filling based on a period of time or an event.

29. The filling system for the enclosed chamber means for claim 28, wherein the period of time can be selected from a group consisting of every hour, everyday, every other day, once a week, every other week, at the end of the shift, at the beginning of the shift, at a maintenance period, other time periods and a combination thereof.

30. The filling system for the enclosed chamber means for claim 28, wherein the event can be selected from a group consisting of before or after the first batch of samples is run, before or after the last batch of samples are run, before or after two batches are run, before or after three batches are run or before or after any other events that is desired by the operator, and a combination thereof.

* * * * *